(12) United States Patent
Luttrull

(10) Patent No.: US 9,308,018 B2
(45) Date of Patent: Apr. 12, 2016

(54) MICROVITREORETINAL SURGERY BLADES

(71) Applicant: Jeffrey K. Luttrull, Ojai, CA (US)

(72) Inventor: Jeffrey K. Luttrull, Ojai, CA (US)

(*) Notice: Subject to any disclaimer, the term of this patent is extended or adjusted under 35 U.S.C. 154(b) by 316 days.

(21) Appl. No.: 13/652,902

(22) Filed: Oct. 16, 2012

(65) Prior Publication Data

US 2013/0096590 A1    Apr. 18, 2013

Related U.S. Application Data

(60) Provisional application No. 61/547,967, filed on Oct. 17, 2011.

(51) Int. Cl.
*A61B 17/32* (2006.01)
*A61B 17/34* (2006.01)
*A61F 9/007* (2006.01)

(52) U.S. Cl.
CPC ......... *A61B 17/3417* (2013.01); *A61F 9/00736* (2013.01); *A61B 2017/3454* (2013.01)

(58) Field of Classification Search
CPC ............... A61B 17/3417; A61B 2017/3454; A61B 17/3211; A61F 9/00736; A61F 9/0133

USPC .................................................. 606/166, 167
See application file for complete search history.

(56) References Cited

U.S. PATENT DOCUMENTS

| | | | |
|---|---|---|---|
| 3,798,688 A | | 3/1974 | Wasson |
| 5,222,967 A | * | 6/1993 | Casebeer et al. .............. 606/166 |
| 5,376,099 A | | 12/1994 | Ellis et al. |
| 5,879,362 A | | 3/1999 | Amann et al. |
| 5,989,262 A | | 11/1999 | Josephberg |
| 7,846,134 B1 | | 12/2010 | Nadolski et al. |
| 2008/0215078 A1 | | 9/2008 | Bennett |
| 2009/0177217 A1 | | 7/2009 | Keller |
| 2010/0100058 A1 | | 4/2010 | Auchter et al. |
| 2010/0139101 A1 | * | 6/2010 | Cooper .......................... 30/153 |

* cited by examiner

*Primary Examiner* — Victor Nguyen
(74) *Attorney, Agent, or Firm* — Kelly & Kelley, LLP

(57) ABSTRACT

A micro-vitreoretinal (MVR) blade for incising tissue for a transvenous chorioretinotomy and similar procedures includes a shaft with a working tip having a chisel-type edge on its end or leading edge. Various embodiments of the inventive MVR blade have different chisel-type edge structures, such as a latitudinal chisel, an angled chisel, a chevron, a reverse chevron, a concave semi-lunar and a guarded or step-down working tip. The MVR blade may also include drug/chemical coatings, electrification or freezing to promote hemostasis or chorioretinal anastomosis formation.

6 Claims, 4 Drawing Sheets

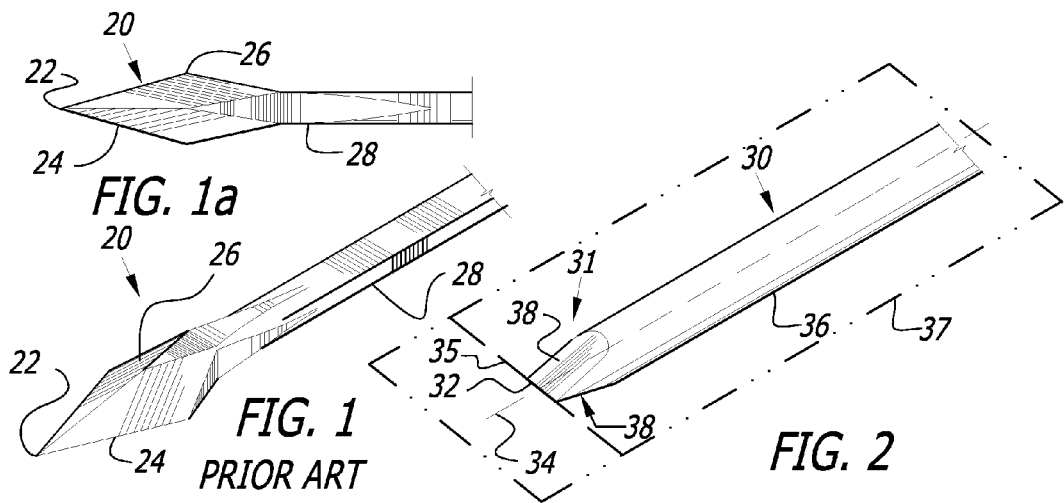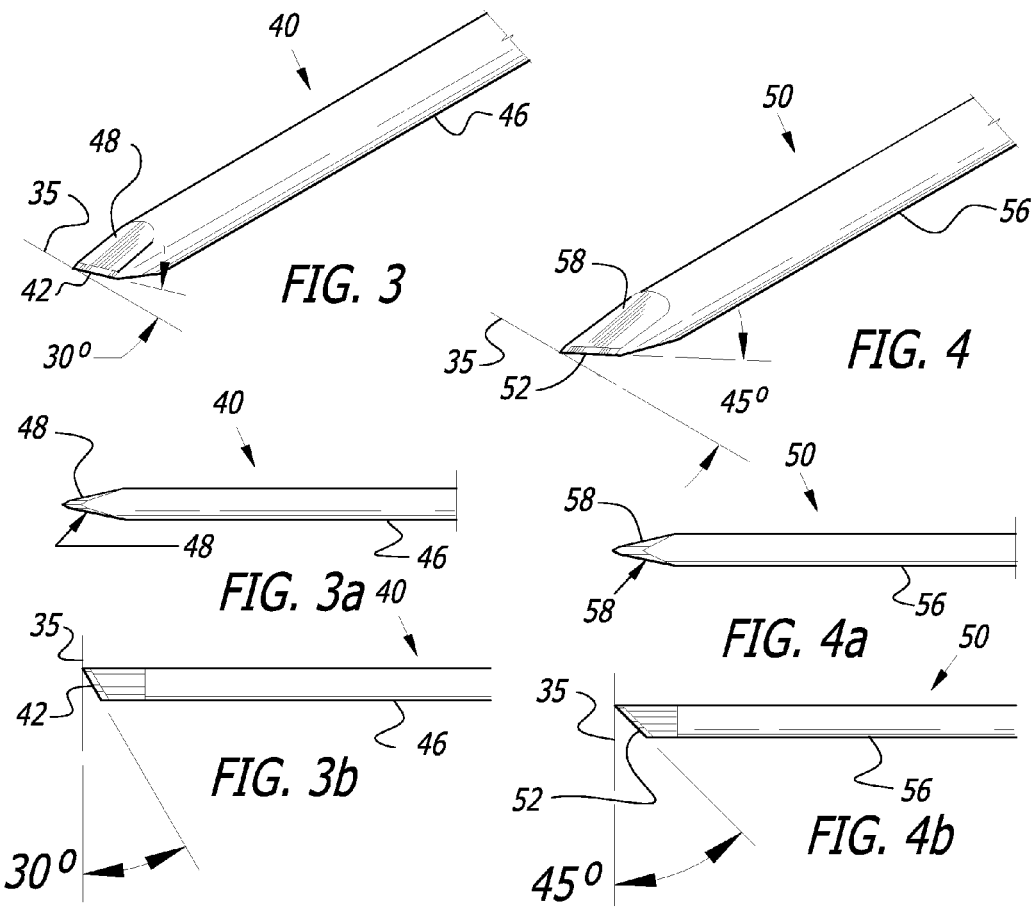

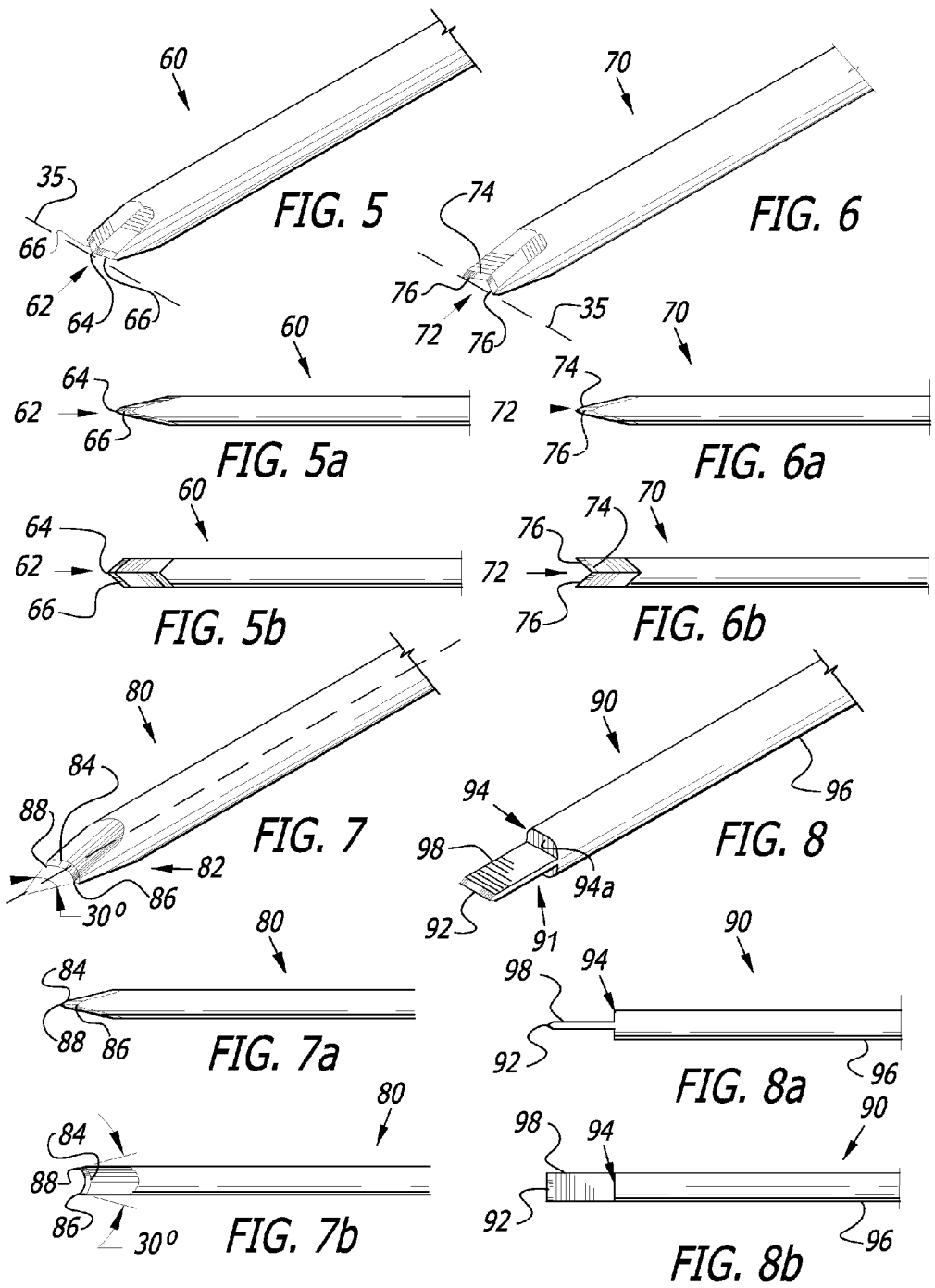

MICROVITREORETINAL SURGERY BLADES

BACKGROUND OF THE INVENTION

The present invention relates generally to incising tissue and in particular to micro-vitreoretinal surgery blades. In just one example, micro-vitreoretinal (MVR) blades are used to incise tissue for a transvenous chorioretinotomy as treatment for retinal vein occlusion and other indications. Retinal vein occlusions are a common cause of visual loss. Currently, the primary treatments are macular laser (for branch retinal vein occlusion) and pharmacologic agents (for branch and central retinal vein occlusion). These treatments address the side-effects of the retinal vein occlusion, including macular edema and ocular neovascularization. Using these conventional treatments for retinal vein occlusion treatment is typically prolonged (months to years) and expensive.

Recently, a new procedure for treating retinal vein occlusions was reported that involves bypassing the occlusion through surgery to create a chorioretinal anastomosis. Unlike previous attempts to perform this same procedure with laser treatments, "pars plana vitrectomy with multiple transvenous chorioretinotomies (MTC) is safer and more effective. This new method reduces or even eliminates the need for continuing medical therapy; improves or stabilizes visual acuity; and reduces the risk of visual loss.

Currently, there is no ideal tool for performing the critical part of the MTC procedure, which is the transvenous chorioretinotomies themselves. Most modern vitreous surgery is performed with 23 or 25 gauge trocar systems, and the prior art MVR blades typically available for such procedures do not function well in MTCs. The drawbacks of such prior art MVR blades include: (a) the blade tips are too narrow, making it difficult to center the blade on the target vein to achieve complete transection; (b) the side edges of the blades are too dull, causing them to displace rather than transect the target vein; and (c) the blade tips are too long, resulting in increased risk of scleral perforation and globe perforation, particularly in myopic patients with thin sclera.

To circumvent the shortcomings of the smaller caliber blades available with trocar-based microincisional viteoretinal surgical systems, it is generally more effective to create an additional incision in the eye (sclerotomy) to allow use of a larger 20 gauge MVR to perform the MTC part of the procedure. The 20 gauge MVR is not hampered by the drawbacks (a) and (b) above. However, the MTC incision it creates is unnecessarily large and use of the 20 gauge blade requires creation of an additional incision in the eye, which adds steps to the procedure, prolonging the surgery and increases the risk of complications.

Accordingly, there is a need for a new MVR blade that addresses these drawbacks. The inventive blade described herein addresses these drawbacks and provides other related advantages.

SUMMARY OF THE INVENTION

The present invention proposes a new MVR knife/blade for use with existing tools in MTC procedures. Overall, the tools would have the same general design as prior art tools of the same type, i.e., shaft, handle, cannula, etc. The tool could also be produced in all gauges popularly used for MVR procedures, including 20, 23, 25 and 27 gauge blades. Unique to the inventive blade is the novel configuration of the cutting tip and edges aimed at addressing the shortcomings described above.

The present invention is directed to a microvitreoretinal blade that has a shaft with a working tip on a distal end thereof. The shaft defines a longitudinal axis and a latitudinal axis. A chisel-type edge is formed on the working tip and disposed in an operative plane formed by the intersection of the longitudinal axis and latitudinal axis. The working tip has two blade surfaces that are disposed on opposite sides of the operative plane and that extend from the shaft to the edge. The chisel-type edge is formed by intersecting edges of the two blade surfaces.

Both the shaft and the working tip preferably have a uniform width throughout the operative plane. In addition, the thickness of the working tip is no greater than the thickness of the shaft in any plane rotated about the longitudinal axis. The chisel-type edge is preferably sharpened to a surgical grade cutting edge.

In various embodiments, the chisel-type edge possesses different configurations. In one preferred embodiment, the chisel-type edge is disposed at an angle of 0 to 45 degrees relative to the latitudinal axis. In another preferred embodiment, the chisel-type edge has a chevron or V-shape with a central point and lateral edges swept back at an angle of 0 to 45 degrees relative to the latitudinal axis. The chisel-type edge may also have a reverse chevron or inverted V-shape with an internal peak and lateral edges swept forward at an angle of 0 to 45 degrees relative to the latitudinal axis. The chisel-type edge may also have a concave, semi-lunar shape with an arc spanning no more than 30 degrees of a circle. Finally, the blade may have a guarded working tip having a step-down from the shaft to the working tip, the step-down forming a stop ledge at the junction of the working tip and the shaft.

The working tip may include a coating to enhance hemostasis or chorioretinal anastomosis. The working tip may also be electrified or brought to freezing temperatures as by liquid nitrogen or similarly known mechanisms to enhance hemostasis or chorioretinal anastomosis.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 1 illustrates a perspective view of a prior art blade typically used for MVR procedures;

FIG. 1a illustrates a top view of a prior art blade typically used for MVR procedures;

FIG. 2 is a perspective view of a first preferred embodiment of an MVR blade of the present invention;

FIG. 3 is a perspective view of a second preferred embodiment of and MVR blade of the present invention;

FIG. 3a is a side view of the second preferred embodiment of an MVR blade of the present invention;

FIG. 3b is a top view of the second preferred embodiment of an MVR blade of the present invention;

FIG. 4 is a perspective view of a third preferred embodiment of and MVR blade of the present invention;

FIG. 4a is a side view of the third preferred embodiment of an MVR blade of the present invention;

FIG. 4b is a top view of the third preferred embodiment of an MVR blade of the present invention;

FIG. 5 is a perspective view of a fourth preferred embodiment of and MVR blade of the present invention;

FIG. 5a is a side view of the fourth preferred embodiment of an MVR blade of the present invention;

FIG. 5b is a top view of the fourth preferred embodiment of an MVR blade of the present invention;

FIG. 6 is a perspective view of a fifth preferred embodiment of and MVR blade of the present invention;

FIG. 6a is a side view of the fifth preferred embodiment of an MVR blade of the present invention;

FIG. 6b is a top view of the fifth preferred embodiment of an MVR blade of the present invention;

FIG. 7 is a perspective view of a sixth preferred embodiment of and MVR blade of the present invention;

FIG. 7a is a side view of the sixth preferred embodiment of an MVR blade of the present invention;

FIG. 7b is a top view of the sixth preferred embodiment of an MVR blade of the present invention;

FIG. 8 is a perspective view of a seventh preferred embodiment of and MVR blade of the present invention;

FIG. 8a is a side view of the seventh preferred embodiment of an MVR blade of the present invention;

FIG. 8b is a top view of the seventh preferred embodiment of an MVR blade of the present invention;

DETAILED DESCRIPTION OF THE PREFERRED EMBODIMENTS

Figure 9:
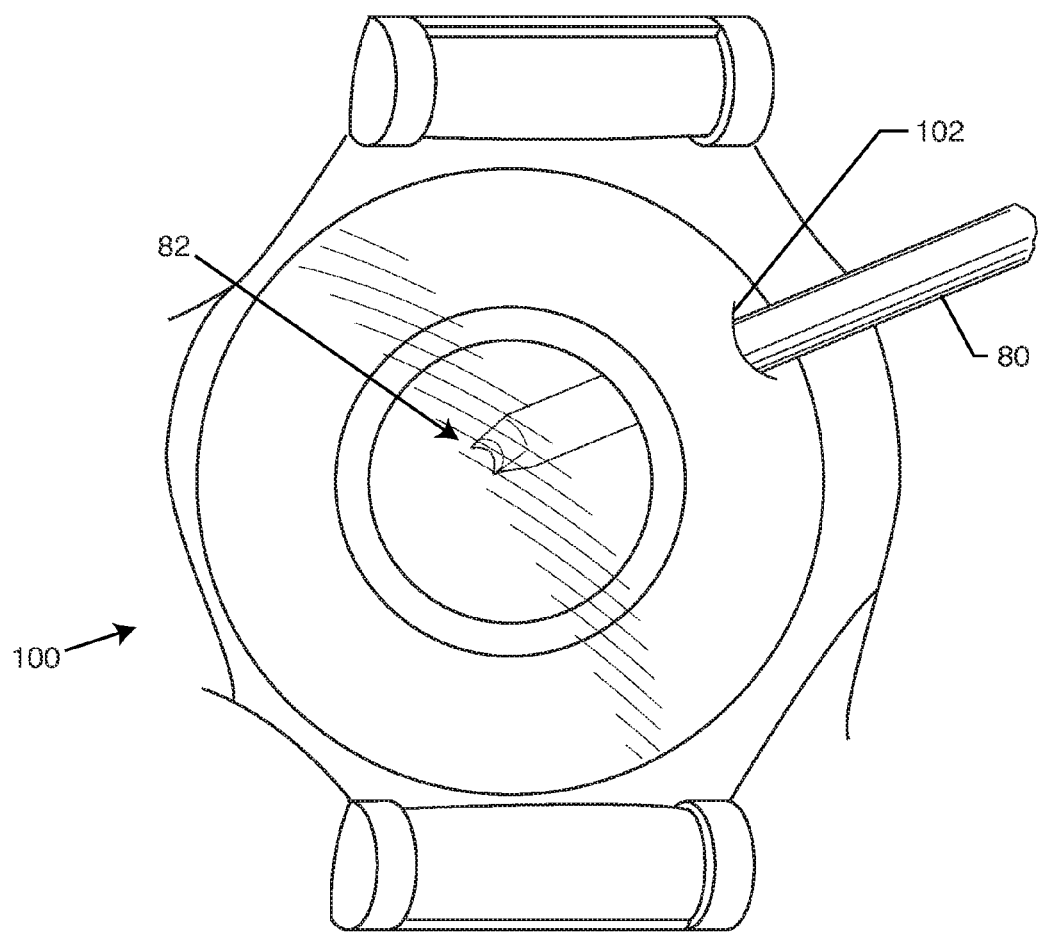
FIG. 9 is an environmental view illustrating insertion of an MVR blade into an eye.

The present invention is directed to novel MVR blades for use in MTC procedures and other similar surgical procedures. In FIGS. 2 through 8, various embodiments of the inventive MVR blades are depicted and referred to by reference numerals 30, 40, 50, 60, 70, 80, and 90. In each embodiment, the differences lie in the shape and configuration of the blade tip—the shaft of each embodiment is generally uniform and configured as the shaft on existing MVR blades.

FIGS. 1 and 1a depict a prior art version of an MVR blade 20 having a stiletto-style geometry, i.e., coming to a sharp point 22 with steep edges 24. The blade 20 has ears 26 with an associated width that is greater than the width of the shaft 28. Such a prior art design is constrained because of how the blade 20 must be ground, such that there is a portion of the blade 20 between the ears 26 and shaft 28 that does not cut tissue. The exaggerated width of the ears 26 also prevents the blade 20 from being fully inserted into or through a 23 or 25 gauge trocar cannula. Prior art MVR blades of smaller gauges, such as 23, 25 and 27, are generally too steep and the edges too blunt for easy and effective transvenous chorioretinotomy.

Rather than having the profile of prior art MVR blades, i.e., very steep, acutely angled edges such as in FIGS. 1 and 1a, the inventive blades are designed with a far less acute blade angle. In addition, some embodiments present a concave cutting edge. These modifications address the above shortcomings by permitting increased ease of centration and "purchase" of the target vein. This provides for more effective and efficient transection by increasing anterior-posterior compression of the target vein coincident with transection and minimizes "escape" of the target vein by lateral displacement.

By increasing the effectiveness and efficiency of the blades, smaller gauge MVR blades can be used in place of the larger gauge blades currently required for microincisional trocar systems, making the additional incisions required for larger blades unnecessary. At the same time, the smaller gauge blades reduce the required size of incisions resulting in reduced recovery time and potential complications from the incision. Finally, the less pointed/less acute angle of the inventive MVR blade minimizes the risk of unnecessarily deep penetration into or through the sclera, while still ensuring complete retinal venous transection and associated chorioretinotomy. Such is required to properly promote the formation of the chorioretinal anastomosis, which will bypass the retinal vein occlusion.

FIG. 2 depicts a first preferred embodiment of the inventive MVR blade 30. In this embodiment, a working tip 31 of the MVR blade 30 has a shape similar to a chisel, i.e., a flat or horizontal chisel-type edge 32 that is generally perpendicular to a longitudinal axis 34 on the shaft 36. As used herein, a "chisel-type edge" means a characteristically flat or planar shaped cutting edge (with some exceptions as described below) on the end or a leading edge of a blade and not on the sides of the blade. A latitudinal axis 35 is disposed perpendicular to the longitudinal axis 34 and is oriented laterally, i.e., side-to-side, with respect to the shaft 36. The intersection of the longitudinal axis 34 and latitudinal axis 35 form an operative plane 37 in which the blade 30 lies. The chisel-type edge 32 is formed by two blade surfaces 38 that extend from the shaft 36 to the chisel-type edge 32. The chisel-type edge 32 is formed where edges of the two blade surfaces 38 intersect.

Both the shaft 36 and the working tip 31 have a uniform width throughout the operative plane 37. In addition, the thickness of the working tip 31 is no greater than the thickness of the shaft in any plane rotated about the longitudinal axis 34. The chisel-type edge 32 is sharpened so as to provide a surgical grade cutting edge. All further embodiments of the inventive MVR blade discussed herein have the same general characteristics, including but not limited to a longitudinal axis 34, a latitudinal axis 35, an operative plane 37, a chisel-type edge, a surgical grade cutting edge, and the width and thickness of the working tip with respect to the shaft.

FIGS. 3, 3a and 3b depict a second preferred embodiment of the inventive MVR blade 40. In this embodiment, the MVR blade 40 again has a shape similar to a chisel, i.e., a chisel-type edge 42, that is generally angled at approximately thirty degrees with respect to the latitudinal axis 35. The chisel-type edge 42 is again formed by the intersecting edge of two blade surfaces 48. One end of the chisel-type edge 42 is then angled back from the latitudinal axis 35 such that it forms a thirty degree angle therewith. The chisel-type edge 42 is sharpened so as to provide a surgical grade cutting tool.

FIGS. 4, 4a and 4b depict a third preferred embodiment of the inventive MVR blade 50. In this embodiment, the MVR blade 50 again has a shape similar to a chisel, i.e., a chisel-type edge 52, that is generally angled at approximately forty-five degrees with respect to the latitudinal axis 35. The chisel-type edge 52 is again formed by the intersecting edges of two blade surfaces 58. One end of the chisel-type edge 52 is then angled back from the latitudinal axis 35 such that it forms a forty-five degree angle therewith. The chisel-type edge 52 is sharpened so as to provide a surgical grade cutting tool.

Between the first, second and third embodiments depicted in FIGS. 2-4, the angle of the chisel-type edge 32, 42, 52 may vary from between zero degrees and forty-five degrees from the latitudinal axis 25. The exact angle that is used can depend upon the specific needs of the surgery being performed.

FIGS. 5, 5a and 5b depict a fourth preferred embodiment of the inventive MVR blade 60. In this embodiment, the MVR blade 60 again has a shape similar to a chisel, except, rather than a horizontal, flat or angled edge, a chevron, i.e., a V-shape, chisel-type edge 62 is presented. The chevron edge 62 comes to a slight point 64 with lateral edges 66 angled or swept back at a slight angle with respect to the latitudinal axis 35. The angle may vary from zero degrees to no more than forty-five degrees from the latitudinal axis 35, but preferably is between zero and thirty degrees. The chevron edge 62 is sharpened so as to provide a surgical grade cutting tool.

FIGS. 6, 6a and 6b depict a fifth preferred embodiment of the inventive MVR blade 70. In this embodiment, the MVR blade 70 again has a shape similar to a chisel, except, rather than a horizontal, flat or angled edge, a reverse chevron, i.e., an inverted V-shape, chisel-type edge 72 is presented. The reverse chevron edge 72 comes to a slight peak 74 with lateral edges 76 angled or swept forward at a slight angle with respect to the latitudinal axis 35. The angle may vary from zero degrees to no more than forty-five degrees from the latitudinal axis 35, but preferably is between zero and thirty degrees. The reverse chevron edge 72 is sharpened so as to provide a surgical grade cutting tool.

FIGS. 7, 7a and 7b depict a sixth preferred embodiment of the inventive MVR blade 80. In this embodiment, the MVR blade 80 again has a shape similar to a chisel, except, rather than a horizontal, flat or angled edge, a concave semi-lunar, i.e., crescent-shape, chisel-type edge 82 is presented. The concave semi-lunar edge 82 has a gradual concave arc 84 that extends smoothly from a first point 86 to a second point 88 of the blade 80 to form the concave semi-lunar edge 82. The arc 84 preferably represents no more than thirty degrees of a complete revolution on a circle. The concave semi-lunar edge 82 is sharpened so as to provide a surgical grade cutting tool.

FIGS. 8, 8a and 8b depict a seventh preferred embodiment of the inventive MVR blade 90, sometimes referred to as a guarded blade or working tip 91. In this embodiment, the MVR blade 90 may have an edge similar to any of the earlier embodiments. FIG. 8 illustrates a thin chisel shape, i.e., a flat or horizontal, chisel-type edge 92, configured similarly to the first embodiment MVR blade 30. The distinguishing feature of this embodiment is the step-down 94, i.e., sudden reduction in cross-sectional width, from the shaft 96 to the blade body 98. The step-down 94 operates to limit the depth of penetration to reduce the risk of scleral perforation or other negative effects of over-insertion. The step-down 94 provides a lip or stop ledge 94a on the end of the shaft 96 that contacts but does not cut or penetrate tissue. It is this contact that stops the cutting motion and prevents over-insertion. Although the blade body 98 may be longer, it is preferably approximately 1 mm-2 mm in length. As in the other embodiments, the chisel-type edge 92 is sharpened so as to provide a surgical grade cutting tool.

FIG. 9 illustrates an environmental view of an MVR blade 80 of the present invention, in this instance the sixth embodiment, penetrating an eye 100 through an incision 102. This and any other similar procedure may be performed with a blade of any other embodiment described herein. In accessing the retina of an eye for performing a transvenous chorioretinotomy or other similar procedures, an MVR blade must pass through the eye 100 in this way and access the retina at the back of the eye 100.

FIGS. 10 through 17 illustrate various views of an MVR blade 80 performing such a transvenous chorioretinotomy procedure. In these illustrations, the interior 100a of the eye is on top and the exterior 100b of the eye is on bottom.

Figure 10:
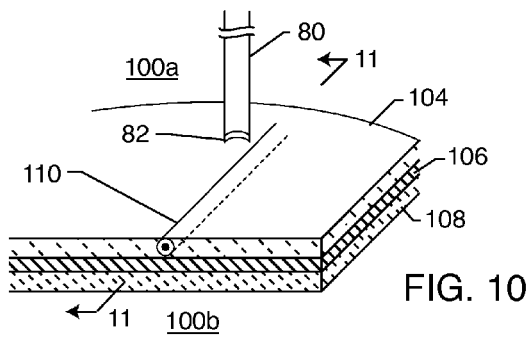
FIG. 10 is an environmental view illustrating an MVR blade approaching an occluded retinal vein preparing to perform a transvenous chorioretinotomy.
Figure 11:
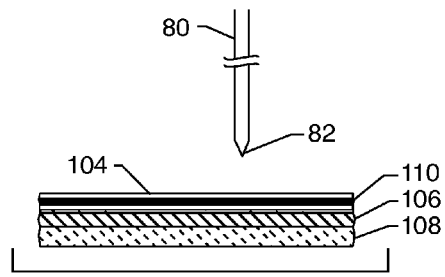
FIG. 11 is a cross-sectional view taken along line 11-11 of FIG. 10.

In FIGS. 10 and 11, the blade 80 is approaching the back of the eye 100, which is comprised of various layers, including the retina 104, the choroid 106 and the sclera 108. The retina 104 contains a vast number of veins 110, of which only one is shown in this illustration for clarity. In performing a transvenous chorioretinotomy, a vein 110 in the retina 104 is occluded or blocked. The healing response to transvenous chorioretinotomy leads to formation of a chorioretinal anastomosis which effectively bypasses the occlusion of the retinal vein.

Figure 12:
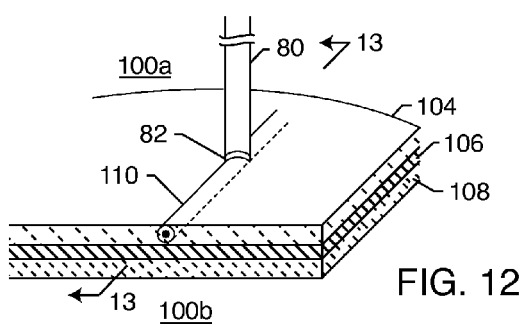
FIG. 12 is an environmental view illustrating an MVR blade contacting an occluded retinal vein preparing to perform a transvenous chorioretinotomy.
Figure 13:
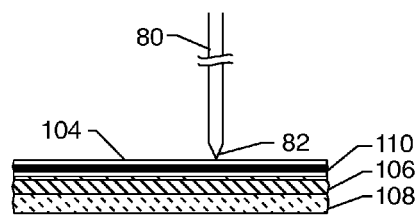
FIG. 13 is a cross-sectional view taken along line 13-13 of FIG. 12.
Figure 14:
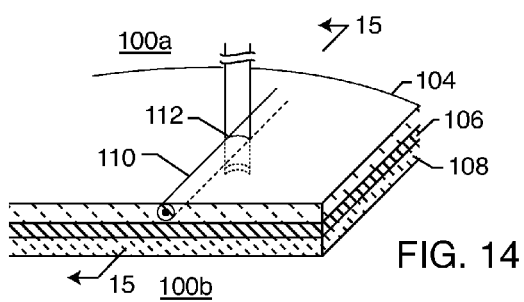
FIG. 14 is an environmental view illustrating an MVR blade transecting an occluded retinal vein after performing a transvenous chorioretinotomy.
Figure 15:
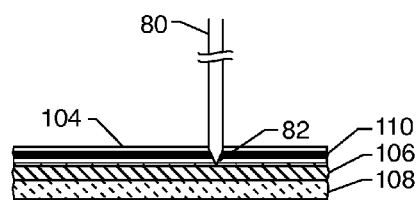
FIG. 15 is a cross-sectional view taken along line 15-15 of FIG. 14.
Figure 16:
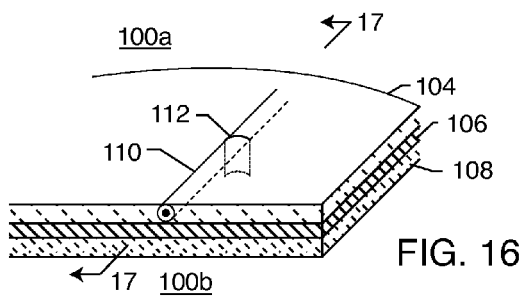
FIG. 16 is an environmental view illustrating a transvenous chorioretinotomy incision after the MVR blade has been removed.
Figure 17:
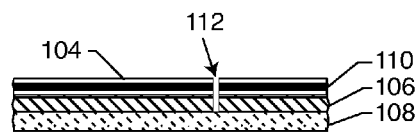
FIG. 17 is a cross-sectional view taken along line 17-17 of FIG. 16.

In FIGS. 12 and 13, the MVR blade 80 has contacted the occluded retinal vein 110. Placement of the blade 80 over the occluded retinal vein 110 is simplified by the concave semi-lunar edge 82, which fixes the blade over the vein 110 preventing displacement of the vein 110 when making the incision. In FIGS. 14 and 15, the MVR blade 80 has incised the tissue and transected the occluded retinal vein 110 only and not the underlying choroid 106 and sclera 108. Insertion of the blade 80 completely transects the occluded retinal vein 110 creating the chorioretinotomy. As illustrated in FIG. 15, the edge 82 of the blade 80 stops upon reaching the choroid 106. In FIGS. 16 and 17, the blade 80 has been withdrawn, leaving an incision 112 that transects the occluded retinal vein 110, as well as the choroid 106 layer underneath. The body's natural healing response results in formation of a chorioretinal anatomosis, which bypasses the blocked retinal vein 110.

Any of the above described blades may be manufactured from any available surgical grade material known in the art. In another embodiment, the blade may be coated with a chemical or drug intended to enhance either (a) hemostasis; or (b) chorioretinal anastomosis formation. Such chemical or drug may comprise a topical thrombogenic and/or anti-thromolytic agent, including, but not limited to, a pharmacologic or mineral blade coating or surface treatment. Such chemicals and/or drugs and methods of coating or treating are known to those skilled in the art. In addition, the blade may be electrified, such as in retinal diathermy, or including a freezing mechanism, such as in retinal cryopexy, to enhance either (a) hemostasis; or (b) chorioretinal anastomosis formation. Methods such as diathermy or cryopexy are standard and long-used methods in such surgical procedures. Cryopexy may be achieved by the use of a probe cooled by liquid nitrogen or other similar agent. Alternatively, one may use a non-cutting probe that is either electrified or features a freezing mechanism to promote chorioretinal anastomosis formation without need for actual tissue incision. Furthermore, any of the above described embodiments may be used to create partial rather than complete transvenous chorioretinotomies for creation of chorioretinal anastomoses.

Certain detailed embodiments of the present invention are disclosed herein. However, it should be understood, that the disclosed embodiments are merely exemplary of the invention, which may be embodied in various forms. Various modifications may be made without departing from the scope and spirit of the invention.

What is claimed is:

1. A microvitreoretinal blade, comprising:
a shaft having a working tip on a distal end, wherein the shaft has a longitudinal axis and a latitudinal axis;
a chisel-type edge on the working tip sharpened to a surgical grade cutting edge and disposed in an operative plane, the operative plane formed by the longitudinal axis and latitudinal axis, wherein the working tip comprises two blade surfaces that are disposed on opposite sides of the operative plane and that extend from the shaft to the edge, the chisel-type edge formed by intersecting edges of the two blade surfaces and being generally perpendicular to the longitudinal axis; and
means for electrifying or freezing the working tip to enhance hemostasis or chorioretinal anastomosis;
wherein both the shaft and the working tip have a uniform width throughout the operative plane, and wherein the thickness of the working tip is no greater than the thickness of the shaft in any plane rotated about the longitudinal axis.

2. The microvitreoretinal blade of claim 1, wherein the chisel-type edge has a chevron or V-shape with a central point and lateral edges swept back at an angle of 0 to 30 degrees relative to the latitudinal axis.

3. The microvitreoretinal blade of claim 1, wherein the chisel-type edge has a reverse chevron or inverted V-shape with an internal peak and lateral edges swept forward at an angle of 0 to 30 degrees relative to the latitudinal axis.

4. The microvitreoretinal blade of claim 1, wherein the chisel-type edge has a concave, semi-lunar shape with an arc spanning no more than 30 degrees of a circle.

5. The microvitreoretinal blade of claim 1, further comprising a coating on the working tip to enhance hemostasis or chorioretinal anastomosis.

6. A microvitreoretinal blade, comprising:
a shaft having a working tip on a distal end, wherein the shaft has a longitudinal axis and a latitudinal axis;
a chisel-type edge on the working tip sharpened to a surgical grade cutting edge and disposed in an operative plane, the operative plane formed by the longitudinal axis and latitudinal axis, wherein the working tip comprises two blade surfaces that are disposed on opposite sides of the operative plane and that extend from the shaft to the edge, the chisel-type edge formed by intersecting edges of the two blade surfaces and being generally perpendicular to the longitudinal axis;
wherein both the shaft and the working tip have a uniform width throughout the operative plane, and wherein the thickness of the working tip is no greater than the thickness of the shaft in any plane rotated about the longitudinal axis; and
wherein the blade comprises a guarded working tip having a step-down from the shaft to the working tip, the step-down forming a fixed stop ledge at the junction of the working tip and the shaft.

* * * * *